(12) United States Patent
Funk et al.

(10) Patent No.: US 8,216,967 B2
(45) Date of Patent: Jul. 10, 2012

(54) METHOD FOR PRODUCING WATER-ABSORBING COMPOSITE MATERIALS

(75) Inventors: Rüdiger Funk, Niedernhausen (DE); Matthias Weismantel, Jossgrund-Oberndorf (DE); Sylvia Bertha, Frankenthal (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/306,193

(22) PCT Filed: Jun. 29, 2007

(86) PCT No.: PCT/EP2007/056571
§ 371 (c)(1),
(2), (4) Date: Jun. 30, 2009

(87) PCT Pub. No.: WO2008/003654
PCT Pub. Date: Jan. 10, 2008

(65) Prior Publication Data
US 2009/0312182 A1    Dec. 17, 2009

(30) Foreign Application Priority Data
Jul. 3, 2006  (EP) .................................... 06116520

(51) Int. Cl.
*B01J 20/26* (2006.01)
*C08F 8/30* (2006.01)

(52) U.S. Cl. .......................... 502/402; 525/178; 525/179
(58) Field of Classification Search .................. None
See application file for complete search history.

(56) References Cited

U.S. PATENT DOCUMENTS

| 7,144,957 B2 | 12/2006 | Funk et al. | |
| 2004/0249079 A1* | 12/2004 | Funk et al. .................... | 525/191 |
| 2006/0025030 A1* | 2/2006 | Funk et al. .................... | 442/118 |

FOREIGN PATENT DOCUMENTS

| WO | WO-03/028778 A2 | 4/2003 |
| WO | WO-03/092757 A1 | 11/2003 |

OTHER PUBLICATIONS

Buchholz et al., *Modern Superabsorbent Polymer Technology*, Wiley-VCH, 71-103 (1998).
Buchholz et al., *Modern Superabsorbent Polymer Technology*, Wiley-VCH, 252-258 (1998).
International Search Report and Written Opinion in PCT/EP2007/056571, dated Nov. 27, 2008.

* cited by examiner

*Primary Examiner* — Melvin C Mayes
*Assistant Examiner* — Bijay Saha
(74) *Attorney, Agent, or Firm* — Marshall, Gerstein & Borun LLP

(57) ABSTRACT

Water-absorbing composites comprising at least two particulate water-absorbing polymers having different pH values and at least one fibrous material are produced without premixing the water-absorbing polymers and are used in hygiene articles.

10 Claims, No Drawings

METHOD FOR PRODUCING WATER-ABSORBING COMPOSITE MATERIALS

CROSS-REFERENCE TO RELATED APPLICATIONS

This is the U.S. national phase application of International Application No. PCT/EP2007/056571, filed Jun. 29, 2007, which claims the benefit of European patent application No. 06116520.5, filed Jul. 3, 2006.

The present invention relates to a process for producing water-absorbing composites comprising at least two particulate water-absorbing polymers having different pH values and at least one fibrous material wherein the water-absorbing polymers are not premixed and their use in hygiene articles.

Further embodiments of the present invention are discernible from the claims, the description and the examples. It will be understood that the hereinbefore mentioned and the hereinbelow still to be more particularly described features of the subject matter of the present invention are utilizable not only in the particular combination indicated but also in other combinations without departing from the realm of the invention.

The production of hygiene articles is described in the monograph "Modern Superabsorbent Polymer Technology", F. L. Buchholz and A. T. Graham, Wiley-VCH, 1998, pages 252 to 258.

Hygiene articles typically consist of a liquid-pervious topsheet (A), a liquid-impersion bottom sheet (B) and a water-absorbing composite (C) between topsheet (A) and bottom sheet (B). Composite (C) consists of water-absorbing polymers and fibers.

The production of water-absorbing polymeric particles is likewise described in the monograph "Modern Superabsorbent Polymer Technology", F. L. Buchholz and A. T. Graham, Wiley-VCH, 1998, pages 71 to 103.

The properties of the water-absorbing polymeric particles can be controlled via the degree of crosslinking. Gel strength increases and absorptive capacity decreases with increasing degree of crosslinking. Consequently, as Absorbency Under Load (AUL) increases, Centrifuge Retention Capacity (CRC) decreases (although toward very high degrees of crosslinking Absorbency Under Load decreases, too).

To improve their performance characteristics, for example Saline Flow Conductivity (SFC) in the diaper and Absorbency Under Load (AUL), water-absorbing polymeric particles are generally postcrosslinked. This increases only the degree of crosslinking of the particle surface, making it possible to decouple Absorbency Under Load (AUL) and Centrifuge Retention Capacity (CRC) to some extent at least. Postcrosslinking can be carried out in the aqueous gel phase. Preferably, however, ground and screened particles of the base polymer are surface coated with a postcrosslinker, dried and thermally postcrosslinked. Useful crosslinkers include compounds comprising at least two groups capable of forming covalent bonds with the carboxylate groups of the hydrophilic polymer.

WO 2003/028778 A2 discloses homogeneous polymeric mixtures of water-absorbing polymeric particles having different pH values.

It is an object of the present invention to provide an improved process for producing water-absorbing composites (C) using particulate water-absorbing polymers having different pH values.

We have found that this object is achieved by a process for producing water-absorbing composites (C) comprising
i) at least one particulate water-absorbing polymer,
ii) at least one further particulate water-absorbing polymer, and
iii) at least one fibrous material,
said polymer i) and said polymer ii) differing by at least 0.5 pH units, which process comprises not premixing said polymer i) and said polymer ii) in a separate operation in the course of the production of said composite (C).

Premixing in a separate operation herein refers to any mixing designed to achieve a homogeneous mixture. Short transportation of the polymer i) and of the polymer ii) in a conjoint conveying line that does not lead to homogeneous commixing shall not be deemed a separate operation for the purposes of this invention.

One preferred embodiment of the present invention comprises transporting polymer i) and polymer ii) for less than 10 m, preferably for less than 5 m, more preferably for less than 1 m and most preferably for less than 0.5 m via a conjoint conveying line.

It is very particularly preferred for the polymers i) and ii) to be conveyed completely separately, i.e., the polymers i) and ii) are separately metered onto the fibrous material iii) and only come into contact with each other in the presence of the fibrous material iii).

The difference in pH between polymer i) and polymer ii) is preferably one pH unit, more preferably 1.5 pH units and most preferably 2.5 pH units, the pH values of the polymers i) and ii) being measured in accordance with German Standard Specification DIN ISO 17190-1:2001.

Polymer i) and/or polymer ii) is preferably a polymer based on at least 50 mol % neutralized acrylic acid.

Polymer i) and/or polymer ii) is preferably in a postcrosslinked state.

The pH of polymer i) is preferably in the range from 3 to 5, more preferably in the range from 3.1 to 3.7 or in the range from 4 to 4.7.

The pH of polymer ii) is preferably in the range from 5.7 to 6.5, more preferably in the range from 5.8 to 6.3 and most preferably in the range from 5.9 to 6.1.

The weight ratio of polymer i) to polymer ii) is preferably in the range from 0.01 to 2, more preferably in the range from 0.05 to 1 and most preferably in the range from 0.1 to 0.5.

The level of fibrous material iii) in the composite (C) is preferably in the range from 10% to 90% by weight, more preferably in the range from 30% to 80% by weight and most preferably in the range from 50% to 70% by weight. Cellulose fibers are the preferred fibrous material iii).

The water-absorbing polymeric particles are obtained for example by polymerization of a monomer solution comprising
a) at least one ethylenically unsaturated acid-functional monomer,
b) at least one crosslinker,
c) if appropriate one or more ethylenically and/or allylically unsaturated monomers copolymerizable with the monomer a), and
d) if appropriate one or more water-soluble polymers onto which the monomers a), b) and if appropriate c) can be at least partly grafted.

Suitable monomers a) are for example ethylenically unsaturated carboxylic acids, such as acrylic acid, methacrylic acid, maleic acid, fumaric acid and itaconic acid or derivatives thereof, such as acrylamide, methacrylamide, acrylic esters and methacrylic esters. Acrylic acid and methacrylic acid are particularly preferred monomers. Acrylic acid is most preferable.

The proportion of the total amount of monomers a) which is attributable to acrylic acid and/or its salts is preferably at least 50% by weight, more preferably at least 70% by weight and most preferably at least 90% by weight.

The monomers a) and especially acrylic acid comprise preferably up to 0.025% by weight of a hydroquinone half ether. Preferred hydroquinone half ethers are hydroquinone monomethyl ether (MEHQ) and/or tocopherols.

Tocopherol refers to compounds of the following formula:

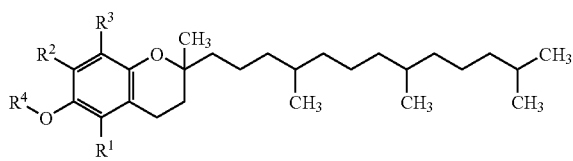

where $R^1$ is hydrogen or methyl, $R^2$ is hydrogen or methyl, $R^3$ is hydrogen or methyl and $R^4$ is hydrogen or an acid radical of 1 to 20 carbon atoms.

Preferred $R^4$ radicals are acetyl, ascorbyl, succinyl, nicotinyl and other physiologically tolerable carboxylic acids. The carboxylic acids can be mono-, di- or tricarboxylic acids.

Preference is given to alpha-tocopherol where $R^1=R^2=R^3$=methyl, especially racemic alpha-tocopherol. $R^1$ is more preferably hydrogen or acetyl. RRR-alpha-Tocopherol is preferred in particular.

The monomer solution comprises preferably not more than 130 weight ppm, more preferably not more than 70 weight ppm, preferably not less than 10 weight ppm, more preferably not less than 30 weight ppm and especially about 50 weight ppm of hydroquinone half ether, all based on acrylic acid, with acrylic acid salts being arithmetically counted as acrylic acid. For example, the monomer solution can be produced using an acrylic acid having an appropriate hydroquinone half ether content.

Crosslinkers b) are compounds having at least two polymerizable groups which can be free-radically interpolymerized into the polymer network. Useful crosslinkers b) include for example ethylene glycol dimethacrylate, diethylene glycol diacrylate, allyl methacrylate, trimethylolpropane triacrylate, triallylamine, tetraallyloxyethane as described in EP 530 438 A1, di- and triacrylates as described in EP 547 847 A1, EP 559 476 A1, EP 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures as described for example in DE 195 43 368 A1, DE 196 46 484 A1, WO 90/15830 A1 and WO 2002/32962 A2.

Useful crosslinkers b) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP 343 427 A2. Useful crosslinkers b) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention may utilize di(meth)acrylates of polyethylene glycols, the polyethylene glycol used having a molecular weight between 300 and 1000.

However, particularly advantageous crosslinkers b) are di- and triacrylates of 3- to 20-tuply ethoxylated glycerol, of 3- to 20-tuply ethoxylated trimethylolpropane, of 3- to 20-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixedly ethoxylated or propoxylated glycerol, of 3-tuply mixedly ethoxylated or propoxylated trimethylolpropane, of 15-tuply ethoxylated glycerol, of 15-tuply ethoxylated trimethylolpropane, of at least 40-tuply ethoxylated glycerol, of at least 40-tuply ethoxylated trimethylolethane and also of at least 40-tuply ethoxylated trimethylolpropane.

Very particularly preferred for use as crosslinkers b) are diacrylated, dimethacrylated, triacrylated or trimethacrylated multiply ethoxylated and/or propoxylated glycerols as described for example in WO 20031104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred.

The amount of crosslinker b) is preferably in the range from 0.01% to 15% by weight, more preferably in the range from 0.5% to 10% by weight and most preferably in the range from 1% to 5% by weight, all based on the monomer solution.

Monomers c) are ethylenically unsaturated monomers that are copolymerizable with the monomers a), examples being acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers d) include polyvinyl alcohol, polyvinylpyrrolidone, starch, starch derivatives, polyglycols or polyacrylic acids, preferably polyvinyl alcohol and starch.

The preferred polymerization inhibitors require dissolved oxygen for optimum performance. Therefore, the polymerization inhibitors may be freed of dissolved oxygen prior to polymerization by inertization, i.e., by flowing an inert gas, preferably nitrogen, through them. The oxygen content of the monomer solution is preferably lowered to less than 1 weight ppm and more preferably less than 0.5 weight ppm prior to polymerization.

The production of a suitable water-absorbing polymeric particle as well as further useful hydrophilic ethylenically unsaturated monomers d) are described in DE 199 41 423 A1, EP 686 650 A1, WO 2001/45758 A1 and WO 2003/104300 A1.

Water-absorbing polymeric particles are typically obtained by addition polymerization of an aqueous monomer solution with or without subsequent comminution of the hydrogel. Suitable methods of making are described in the literature. Water-absorbing polymers are obtainable for example by:

gel polymerization in a batch process or tubular reactor and subsequent comminution in meat grinder, extruder or kneader (EP 445 619 A2, DE 19 846 413 A1), addition polymerization in kneader with continuous comminution by contrarotatory stirring shafts for example (WO 2001/38402 A1), addition polymerization on belt and subsequent comminution in meat grinder, extruder or kneader (DE 38 25 366 A1, U.S. Pat. No. 6,241,928), emulsion polymerization to produce bead polymers having a relatively narrow gel size distribution (EP 457 660 A1).

The reaction is preferably carried out in a kneader as described for example in WO 2001/38402 A1, or on a belt reactor as described for example in EP 955 086 A2.

The acid groups of the hydrogels obtained are typically in a partially neutralized state, the extent of neutralization being preferably in the range from 25 to 85 mol %, more preferably in the range from 27 to 80 mol %, even more preferably in the range from 27 to 30 mol % or in the range from 40 to 75 mol %, for which the customary neutralizing agents can be used, preferably alkali metal hydroxides, alkali metal oxides, alkali metal carbonates or alkali metal bicarbonates and also mixtures thereof. Ammonium salts can also be used instead of alkali metal salts. Sodium and potassium are particularly preferred as alkali metals, but most preference is given to sodium hydroxide, sodium carbonate or sodium bicarbonate and also mixtures thereof. Typically, neutralization is achieved by admixing the neutralizing agent as an aqueous solution or else preferably as a solid. For example, sodium hydroxide having a water content of distinctly below 50% by weight can be present as a waxy mass having a melting point above 23° C. In this case, metering as piece goods or melt at elevated temperature is possible.

Neutralization can be carried out after polymerization, at the hydrogel stage. But it is also possible to neutralize up to 40 mol %, preferably from 10 to 30 mol % and more preferably from 15 to 25 mol % of the acid groups before polymerization by adding a portion of the neutralizing agent to the monomer solution and setting the desired final degree of neutralization only after polymerization, at the hydrogel stage. The monomer solution can be neutralized by admixing the neutralizing agent. The hydrogel may be mechanically comminuted, for example by means of a meat grinder, in which case the neutralizing agent can be sprayed, sprinkled or poured on and then carefully mixed in. To this end, the gel mass obtained can be repeatedly meat-grindered for homogenization. Neutralization of the monomer solution to the final degree of neutralization is preferred.

The neutralized hydrogel is then dried with a belt or drum dryer until the residual moisture content is preferably below 15% by weight and especially below 10% by weight, the water content being determined in a accordance with German Standard Specification DIN ISO 17190-4:2001. Selectively, drying can also be carried out using a fluidized bed dryer or a heated plowshare mixer. To obtain particularly white products, it is advantageous to dry this gel by ensuring rapid removal of the evaporating water. To this end, the dryer temperature must be optimized, the air feed and removal has to be policed, and at all times sufficient venting must be ensured. Drying is naturally all the more simple—and the product all the more white—when the solids content of the gel is as high as possible. The solids content of the gel prior to drying is therefore preferably between 30% and 80% by weight. It is particularly advantageous to vent the dryer with nitrogen or some other nonoxidizing inert gas. Selectively, however, simply just the partial pressure of the oxygen can be lowered during drying to prevent oxidative yellowing processes. But in general adequate venting and removal of the water vapor will likewise still lead to an acceptable product. A very short drying time is generally advantageous with regard to color and product quality.

The dried hydrogel is preferably ground and sieved, useful grinding apparatus typically including roll mills, pin mills or swing mills. The particle size of the sieved, dry hydrogel is preferably below 1000 µm, more preferably below 900 µm and most preferably below 850 µm and preferably above 80 µm, more preferably above 90 µm and most preferably above 100 µm.

Very particular preference is given to a particle size (sieve cut) in the range from 150 to 850 µm. Particle size is determined in accordance with German Standard Specification DIN ISO 17190-3:2001.

The water-absorbing polymeric particles are subsequently postcrosslinked. Useful postcrosslinkers are compounds comprising two or more groups capable of forming covalent bonds with the carboxylate groups of the hydrogel. Suitable compounds are for example alkoxysilyl compounds, polyaziridines, polyamines, polyamidoamines, di- or polyepoxides, as described in EP 83 022 A2, EP 543 303 A1 and EP 937 736 A2, di- or polyfunctional alcohols, as described in DE 33 14 019 A1, DE 35 23 617 A1 and EP 450 922 A2, or β-hydroxyalkylamides, as described in DE 102 04 938 A1 and U.S. Pat. No. 6,239,230.

Furthermore, DE 40 20 780 C1 describes cyclic carbonates, DE 198 07 502 A1 2-oxazolidone and its derivatives, such as 2-hydroxyethyl-2-oxazolidone, DE 198 07 992 C1 bis- and poly-2-oxazolidinones, DE 198 54 573 A1 2-oxotetrahydro-1,3-oxazine and its derivatives, DE 198 54 574 A1 N-acyl-2-oxazolidones, DE 102 04 937 A1 cyclic ureas, DE 103 34 584 A1 bicyclic amide acetals, EP 1 199 327 A2 oxetanes and cyclic ureas and WO 2003/31482 A1 morpholine-2,3-dione and its derivatives as useful postcrosslinkers.

Polyvalent cations are advantageously used for surface postcrosslinking as well as surface postcrosslinkers. Useful polyvalent cations include for example bivalent cations, such as the cations of zinc, magnesium, calcium and strontium, tervalent cations, such as the cations of aluminum, iron, chromium, rare earths and manganese, quadruvalent cations, such as the cations of titanium and zirconium. Useful counterions include chloride, bromide, sulfate, hydrogensulfate, carbonate, bicarbonate, nitrate, phosphate, hydrogenphosphate, dihydrogenphosphate and carboxylate, such as acetate and lactate. Aluminum sulfate is preferred.

Postcrosslinking is typically carried out by spraying a solution of the surface postcrosslinker onto the hydrogel or onto the dry polymeric powder. The surface postcrosslinker and the polyvalent cation can be spray dispensed in a conjoint solution or as separate solutions. After spraying, the polymeric powder is thermally dried, and the crosslinking reaction can take place not only before but also during drying.

The spraying with a solution of the postcrosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Useful mixers include for example Lödige® mixers, Bepex® mixers, Nauta® mixers, Processall® mixers and Schugi® mixers. Very particular preference is given to employing high speed mixers, for example of the Schuggi-Flexomix® or Turbolizer® type.

Contact dryers are preferable, shovel dryers more preferable and disk dryers most preferable as apparatus in which thermal postcrosslinking is carried out. Useful dryers include for example Bepex® dryers and Nara® dryers, Fluidized bed dryers can be used as well.

Postcrosslinking can take place in the mixer itself, by heating the jacket or by blowing warm air into the mixer. Also suitable is a downstream dryer, for example a tray dryer, a rotary tube oven or a heatable screw. But it is also possible to utilize for example an azeotropic distillation as a drying process.

Heat is preferably supplied indirectly, more preferably by heat of condensation and most preferably by condensation of water vapor. To this end, the outside wall of the postcrosslinking apparatus is brought into contact with a suitable heat transfer medium, for example a hot gas which condenses on the wall and thereby releases its heat of condensation to the wall.

After postcrosslinking, the water-absorbing polymeric particles are typically subjected to active cooling, preferably to a temperature of less than 120° C., more preferably less than 100° C. and most preferably less than 80° C.

The Centrifuge Retention Capacity of water-absorbing polymers is typically in the range from 25 to 60 g/g, preferably at least 30 g/g, more preferably at least 32 g/g, even more preferably at least 34 g/g and most preferably at least 35 g/g. Centrifuge Retention Capacity (CRC) is determined in accordance with German Standard Specification DIN ISO 17190-6:2001.

The water-absorbing composite (C), as well as the water-absorbing polymeric particles i) and ii), comprises at least one, preferably hydrophilic, fibrous material iii). Hydrophilic is to be understood as meaning that aqueous fluids are rapidly distributed over the fiber. Usually the fibrous material is cellulose, modified cellulose, rayon, polyester such as polyethylene terephthalate. Particular preference is given to cellulose fibers such as chemical pulp. Fiber diameter is generally in the range from 1 to 200 μm and preferably in the range from 10 to 100 μm. Fiber length is at least 1 mm.

Generally it is possible to fix polymeric particles within the composite (C) to improve dry and wet integrity. Dry and wet integrity describes the ability to install water-absorbing polymeric particles in the composite (C) such that they withstand external forces not only in the wet state but also in the dry state and that water-absorbing polymeric particles do not dislocate or spill out. The forces referred to are, in particular, mechanical stresses as occur in the course of moving about while wearing a hygiene article or else the weight pressure in the hygiene article in the case of incontinence in particular. As to fixation, one skilled in the art will know a multiplicity of possibilities. Examples such as fixation by heat treatment, addition of adhesives, thermoplastics, binder materials are noted in the patent application WO 95/26209 A1 page 37 line 36 to page 41 line 14. The identified said passage is thus part of this invention. Methods of enhancing wet strength are also to be found in the patent application WO 00/36216 A1.

The construction of the present invention's composite (C) is based on various fibrous materials, which are used as a network of fibers or as matrices. The present invention includes not only fibers of natural origin (modified or unmodified) but also synthetic fibers.

A detailed overview of examples of fibers which can be used in the present invention is given by the patent application WO 95/26209 A1 page 28 line 9 to page 36 line 8. Said passage is thus part of this invention.

Examples of cellulose fibers include those customarily used in absorbent products, such as fluff pulp and chemical pulp of the cotton type. The materials (softwoods or hardwoods), production processes, such as chemical pulp, semi-chemical pulp, chemothermal mechanical pulp (CTMP) and bleaching processes are not particularly restricted. For instance, natural cellulosic fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers, and also bicomponent fibers composed of polyethylene terephthalate-polyethylene isophthalate copolymer, polyethyl vinyl acetate-polypropylene, polyethylene-polyester, polypropylene-polyester, copolyester-polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhering bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter will migrate to some extent into the matrix of the fibrous material present and so constitute bond sites and renewed stiffening elements on cooling. Additionally the addition of thermoplastic fibers means that there is an increase in the pore dimensions present after the heat treatment has taken place. This makes it possible, by continuous addition of thermoplastic fibers during the formation of the absorbent layer, to continuously increase the fraction of thermoplastic fibers in the direction of the topsheet, and this results in a similarly continuous increase in pore sizes. Thermoplastic fibers can be formed from a multiplicity of thermoplastic polymers which have a melting point of less than 190° C. and preferably in the range from 75 to 175° C. These temperatures are too low for damage to the cellulose fibers to be likely.

Lengths and diameters of the synthetic fibers described above are not particularly restricted, and generally any desired fiber from 1 to 200 mm in length and from 0.1 to 100 denier (gram per 9000 meters) in diameter may preferably be used. Preferred thermoplastic fibers are from 3 to 50 mm in length and more preferably from 6 to 12 mm in length. The preferred diameter for the thermoplastic fiber is between 1.4 and 10 decitex, more preferably between 1.7 and 3.3 decitex (gram per 10 000 meters). The form is not particularly restricted and examples include woven types, narrow cylindrical types, cut/split yarn types, staple fiber types and continuous filament fiber types.

Suitable hydrophilic fibers for use in the present invention's water-absorbing composites (C) include for example cellulose fibers, modified cellulose fibers, rayon, polyester fibers such as for example polyethylene terephthalate (DACRON®) and hydrophilic nylon (HYDROFIL®). Suitable hydrophilic fibers are also obtainable by hydrophilicizing hydrophobic fibers, for example by the treatment of thermoplastic fibers obtained from polyolefins (for example polyethylene or polypropylene, polyamides, polystyrenes, polyurethanes, etc.) with surfactants or silica. However, for cost reasons and ease of availability, cellulose fibers are preferred.

The water-absorbing polymeric particles are embedded in the fibrous material described. This can be accomplished in various ways, for example by using the hydrogel material and the fibers together to construct an absorbent layer in the form of a matrix, or by installing water-absorbing polymeric particles in layers of fibrous mixture, where they are ultimately fixed, whether by means of bonding agent or by lamination of the layers.

The fluid-acquiring and -distributing fibrous matrix may consist of synthetic fiber or cellulose fiber or of a mixture of synthetic fiber and cellulose fiber, in which case the mixing ratio may vary from (100 to 0) synthetic fiber: (0 to 100) cellulose fiber. The cellulose fibers used may additionally have been chemically stiffened to increase dimensional stability.

The chemical stiffening of cellulose fibers may be provided in various ways. A first way of providing fiber stiffening is by adding suitable coatings to the fibrous material. Such additions include for example polyamide-epichlorohydrin coatings (Kymene® 557H, Hercules, Inc. Wilmington Del., USA), polyacrylamide coatings (described in U.S. Pat. No. 3,556,932 or as the Parez® 631 NC commercial product from American Cyanamid Co., Stamford, Conn., USA), melamine-formaldehyde coatings and polyethyleneimine coatings.

Cellulose fibers can also be chemically stiffened by chemical reaction. For instance, suitable crosslinker substances can be added to effect crosslinking taking place within the fiber. Suitable crosslinker substances are typical substances used for crosslinking monomers, including but not limited to $C_2$-$C_8$ dialdehydes, $C_2$-$C_8$ monoaldehydes having acidic functionality, in particular $C_2$-$C_9$ polycarboxylic acids.

Specific substances from this series are for example glutaraldehyde, glyoxal, glyoxylic acid, formaldehyde and citric acid. These substances react with at least two hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162 A1, U.S. Pat. Nos. 3,224,926, 3,440,135, 3,932,209, 4,035,147, 4,822,453, 4,888,093, 4,898,642 and 5,137,537. The chemical crosslinking imparts stiffening to the fibrous material, which is ultimately reflected in improved dimensional stability for the hygiene article as a whole. The individual layers are joined together by methods known to one skilled in the art, for example intermelting by heat treatment, addition of hot-melt adhesives, latex binders, etc.

Examples of processes whereby a water-absorbing composite (C) is obtained which consist for example of a backing material to which water-absorbing polymeric particles are fixed one- or both-sidedly are known and included by the invention, but not limited thereto.

Examples of processes to obtain a water-absorbing composite (C) which consists for example of water-absorbing polymeric particles (c) embedded in a fibrous material mixture of synthetic fibers (a) and cellulose fibers (b), for which the mixing ratio can vary from (100 to 0) synthetic fiber: (0 to 100) cellulose fiber, include (1) a process wherein (a), (b) and (c) are mixed at one and the same time, (2) a process wherein a mixture of (a) and (b) is mixed into (c), (3) a process wherein a mixture of (b) and (c) is mixed with (a), (4) a process wherein a mixture of (a) and (c) is mixed into (b), (5) a process wherein (b) and (c) are mixed and (a) is continuously metered in, (6) a process wherein (a) and (c) are mixed and (b) is continuously metered in, and (7) a process wherein (b) and (c) are mixed separately into (a). Of these examples, processes (1) and (5) are preferred. Apparatus used in this process is not particularly restricted and any customary apparatus known to one skilled in the art can be used.

The correspondingly produced a water-absorbing composite (C) can optionally be subjected to a heat treatment, so that an absorbent layer having excellent dimensional stability in the moist state is obtained. The heat treatment process is not particularly restricted. Examples include heat treatment by feeding hot air or infrared radiation. The temperature of the heat treatment is in the range from 60° C. to 230° C., preferably between 100° C. and 200° C. and more preferably between 100° C. and 180° C.

The duration of the heat treatment depends on the identity of the synthetic fiber, its amount and the hygiene article production rate. In general, the duration of the heat treatment is between 0.5 seconds to 3 minutes and preferably 1 second to 1 minute.

The water-absorbing composite (C) is generally provided for example with a liquid-pervious topsheet and a liquid-impervious backsheet. Furthermore, leg cuffs and adhesive tabs are attached to finalize the hygiene article. The materials and types of pervious topsheet and impervious backsheet and also of the leg cuffs and adhesive tabs are known to one skilled in the art and are not particularly restricted. Examples thereof are found in WO 95/26209 A1.

The present invention further provides for the use of the abovementioned water-absorbing composites (C) in hygiene articles. The hygiene article can be constructed for example as follows:

(A) a liquid-pervious topsheet,
(B) a liquid-impervious bottom sheet,
(C) the composite between topsheet (A) and bottom sheet (B),
(D) selectively a tissue layer situated directly above and below the composite (C), and
(E) selectively an acquisition layer situated between topsheet (A) and composite (C).

Hygiene articles herein include for example incontinence pads and incontinence briefs for adults or diapers for babies.

The liquid-pervious topsheet (A) is the layer in direct contact with the skin. The material therefore consists of customary synthetic or semisynthetic fibers or films of polyester, polyolefins, rayon or natural fibers such as cotton. In the case of non-woven materials, the fibers must generally be bonded together by means of binders such as polyacrylates. Preferred materials are polyester, rayon and blends thereof, polyethylene and polypropylene. Examples of liquid-pervious layers are described in WO 99/57355 A1, EP-A 1 023 883.

The liquid-impervious layer (B) consists in general of a film of polyethylene or polypropylene.

The water-absorbing composites (C) produced according to the process of the present invention possess improved Absorbency Under Load (AUL) and improved Saline Flow Conductivity (SFC) compared with the composites (C) produced according to hitherto customary processes.

Methods:

The measurements should be carried out unless otherwise stated at an ambient temperature of 23±2° C. and a relative humidity of 50±10%. The water-absorbing compositions are thoroughly commixed before measurement.

Centrifuge Retention Capacity (CRC)

Centrifuge retention capacity of water-absorbing polymeric particles is determined in accordance with German Standard Specification DIN ISO 17190-6:2001.

Absorbency Under Load AUL0.3 psi

Absorbency under a load of 0.3 psi (2070 Pa) of water-absorbing composites (C) is determined analogously to German Standard Specification DIN ISO 17190-7:2001. To this end, a circularly round piece 60 mm in diameter is die cut out of the composite (C). The tissue layers are subsequently removed.

Absorbency Under Load AUL0.7 psi

Absorbency under a load of 0.7 psi (4830 Pa) of water-absorbing composites is determined similarly to absorbency under a load of 0.3 psi (2070 Pa).

Saline Fluid Conductivity (SFC)

Saline fluid conductivity of a swollen layer of gel under a confining pressure of 0.3 psi (2070 Pa) is determined similarly to the method described in EP 640 330 A1 as a swollen gel layer permeability.

The apparatus described in the aforementioned patent application on page 19 and in FIG. 8 is modified to the effect that the glass frit (40) is no longer used, the piston (39) is made of the same plastics material as the cylinder (37) and now comprises 21 equally sized holes uniformly distributed over the entire contact surface. The procedure and also evaluation of the measurement remains unchanged compared with EP 0 640 330 A1. Flow rate is recorded automatically.

Water-absorbing composites (C) are used instead of the water-absorbing polymeric particles used in EP 640 330 A1. A circularly round piece 60 mm in diameter is die cut out of the composite (C) for this purpose. The tissue layers are subsequently removed.

Saline flow conductivity (SFC) is calculated as follows:

$$\text{SFC } [cm^3 s/g] = (Fg(t=0) \times L0)/(d \times A \times WP),$$

where $Fg(t=0)$ is the flow rate of NaCl solution in g/s obtained from a linear regression analysis of the $Fg(t)$ data of the flow rate determinations by extrapolation to $t=0$, $L0$ is the thickness of the gel layer in cm, $d$ is the density of the NaCl solution in $g/cm^3$, $A$ is the area of the gel layer in $cm^2$, and WP is the hydrostatic pressure above the gel layer in $dyn/cm^2$.

EXAMPLES

Example 1

Production of Water-absorbing Polymer (Degree of Neutralization 40 mol %)

2.59 kg of a 37.3% by weight aqueous sodium acrylate solution were mixed with 1.11 kg of acrylic acid, 2.20 kg of water, 0.55 g of sorbitan monolaureate and 2.8 g of urea and inertized with nitrogen. This mixture was filled into a nitrogen-inertized Werner & Pfleiderer LUK 8.0 K2 kneader (2 sigma screws) and admixed in succession with 4.4 g of polyethylene glycol diacrylate 400 (diacrylate of a polyethylene glycol having an average molecular weight of 400 g/mol), 3.7 g of a 0.5% by weight aqueous ascorbic acid solution, 9.4 g of a 15% by weight aqueous sodium persulfate solution and 3.7 g of a 2.5% by weight aqueous hydrogen peroxide solution. The kneader was stirred at maximum speed (98 rpm for the faster screw, about 49 rpm for the slower screw, ratio about 2:1). Immediately following addition of hydrogen peroxide, the kneader jacket was heated with hot heat transfer medium at 80° C. Upon attainment of the maximum temperature, the jacket heating was switched off and the kneader was allowed to react for a further 15 minutes. The gel was cooled down to 65° C. and removed from the kneader. The gel was dried at 140° C. for 90 minutes with a load of 700 g per tray in a circulating air drying cabinet. After threefold grinding in a roll mill (Gebr. Baumeister LRC 125/70, nip width 1000 µm, 600 µm, 400 µm), the polymer was screened to a sieve cut between 850 and 100 µm.

1200 g of this polymer were transferred into a Gebr. Lödige laboratory mixer (M5R type). At 23° C., a mixture of 5.4 g of 1,2-propanediol, 0.4 g of diethylene glycol diglycidyl ether and 21.4 g of water were sprayed onto the polymer via a nozzle. The mixer was subsequently fast heated to 146° C. and maintained at 146° C. for 30 minutes. After cooling, the polymer was screened off to a sieve cut between 850 and 100 µm.

Centrifuge retention capacity (CRC) of the postcrosslinked water-absorbing polymeric particles was 24.8 g/g.

Example 2

Production of Water-absorbing Polymer (Degree of Neutralization 70 mol %)

4.62 kg of a 37.3% by weight aqueous sodium acrylate solution were mixed with 566 g of acrylic acid and 692 g of water and inertized with nitrogen. This mixture was filled into a nitrogen-inertized Werner & Pfleiderer LUK 8.0 K2 kneader (2 sigma screws) and admixed in succession with 10.2 g of 15-tuply ethoxylated trimethylolpropane triacrylate, 15.8 g of a 0.5% by weight aqueous ascorbic acid solution, 18.9 g of a 15% by weight aqueous sodium persulfate solution and 0.68 g of a 2.5% by weight aqueous hydrogen peroxide solution. The kneader was stirred at maximum speed (98 rpm for the faster screw, about 49 rpm for the slower screw, ratio about 2:1). Immediately following addition of hydrogen peroxide, the kneader jacket was heated with hot heat transfer medium at 80° C. Upon attainment of the maximum temperature, the jacket heating was switched off and the kneader was allowed to react for a further 15 minutes. The gel was cooled down to 65° C. and removed from the kneader. The gel was dried at 160° C. for 90 minutes with a load of 700 g per tray in a circulating air drying cabinet. After threefold grinding in a roll mill (Gebr. Baumeister LRC 125/70, nip width 1000 µm, 600 µm, 400 µm), the polymer was screened to a sieve cut between 850 and 100 µm.

1200 g of this polymer were transferred into a Gebr. Lödige laboratory mixer (M5R type). At 23° C., a mixture of 12 g of isopropanol, 0.8 g of oxazolidin-2-one and 24 g of water were sprayed onto the polymer via a nozzle. The mixer was subsequently fast heated to 180° C. and maintained at this temperature for 30 minutes. After cooling, the polymer was screened off to a sieve cut between 850 and 100 µm.

Centrifuge retention capacity (CRC) of the postcrosslinked water-absorbing polymeric particles was 31.0 g/g.

Example 3

Production of Water-absorbing Composite (According to Invention)

3.5 g of water-absorbing polymeric particles from Example 1 were weighed out into six equal portions of 0.583±0.001 g on weighing boats.

3.5 g of water-absorbing polymeric particles from Example 2 were weighed out into six equal portions of 0.583±0.001 g on weighing boats.

2.5 g of cellulose fluff were divided into six equal portions of 0.42±0.01 g.

The water-absorbing composite (C) was produced as follows:

A tissue (SCA Hygiene Products AB, Sweden) is placed on a rectangular wire mesh 17.5 cm in length and 11 cm in width in such a way that the tissue extends somewhat beyond the wire mesh. The wire mesh is situated underneath a perpendicular shaft of the same dimensions. In this shaft, at a point about 75 cm above the wire mesh, a longitudinally installed brush rotates. The brush is 17.5 cm in length and 10 cm in diameter. The brush rotates at 13.5 revolutions per second. Vacuum was applied underneath the wire mesh bearing the tissue.

The first portion of cellulose fluff was applied downwardly to the rotating brush. After 25 seconds, the first portion of polymer of Example 1 and the first portion of polymer of Example 2 were simultaneously metered downwardly onto the rotating brush.

The additions of cellulose fluff and water-absorbing polymeric particles were repeated in total two more times after every 25 seconds. The wire mesh with the tissue was then turned horizontally about 180°.

The additions of cellulose fluff and water-absorbing polymeric particles were then repeated three more times altogether, and the resulting water-absorbing composite (C) was compressed by hand using a piston 15 cm in length and 8.5 cm in width, removed from the tissue and wrapped in a tissue (SCA Hygiene Products, AB, Sweden) 37 cm in length and 24 cm in width.

Absorbency under load (AUL0.3 psi and AUL0.7 psi) and saline flow conductivity (SFC) were determined. The results are summarized in table 1.

Example 4

Production of Water-absorbing Composite (not According to Invention)

A mixture of water-absorbing polymeric particles was produced using a laboratory scale tumble mixer. The mixture comprised 50% by weight of polymer of Example 1 and 50% by weight of polymer of Example 2.

7.0 g of the polymer mixture obtained were weighed out as six equal portions of 1.167±0.001 g on weighing boats.

The water-absorbing composite (C) was produced similarly to Example 3. The water-absorbing polymeric particles of Examples 1 and 2 were added in premixed form.

Absorbency under load (AUL0.3 psi and AUL0.7 psi) and saline flow conductivity (SFC) were determined. The results are summarized in Table 1.

TABLE 1

Results

| Example | Water-absorbing polymer | AUL0.3 psi [g/g] | AUL0.7 psi [g/g] | SFC [$10^{-7} \times cm^3 s/g$] |
|---|---|---|---|---|
| 3 | Example 1 + Example 2 not premixed | 22.6 | 17.3 | 24 |
| 4 (comp.) | Example 1 + Example 2 premixed | 21.8 | 16.8 | 19 |

We claim:

1. A process for producing a water-absorbing composite comprising
   i) at least one particulate water-absorbing polymer,
   ii) at least one further particulate water-absorbing polymer, and
   iii) at least one fibrous material selected from the group consisting of a cellulose fiber and a synthetic fiber,
   said polymer i) and said polymer ii) differing by at least 0.5 pH units, as measured in accordance with German Standard Specification DIN ISO 17190-1:2001, which process comprises admixing i), ii), and iii), wherein said polymer i) and said polymer ii) are separately added during admixing in the absence of premixing of said polymer i) with said polymer ii) in a separate operation prior to the admixing of i), ii), and iii).

2. The process according to claim 1 wherein said polymer i) and/or said polymer ii) is a polymer based on at least 50 mol % neutralized acrylic acid.

3. The process according to claim 1 wherein said polymer i) and/or said polymer ii) is in a postcrosslinked state.

4. The process according to claim 1 wherein said polymer i) has a pH in the range from 3 to 5.

5. The process according to claim 1, wherein said polymer ii) has a pH in the range from 5.7 to 6.5.

6. The process according to claim 1 wherein the weight ratio of said polymer i) to said polymer ii) is in a range from 0.01 to 2.

7. The process according to claim 1 wherein said composite comprises 10% to 90% by weight of said fibrous material iii).

8. The process according to claim 1 wherein said fibrous material iii) consists of cellulose fibers.

9. A composite prepared by the process of claim 1.

10. A hygiene article comprising a composite prepared by the process of claim 1.

* * * * *